United States Patent
Song

(12) 
(10) Patent No.: US 6,773,725 B1
(45) Date of Patent: Aug. 10, 2004

(54) COMPOSITION FOR INCREASING PRESERVATIVE CAPABILITY AND PROMOTING THE GROWTH OF LIVING ORGANISM AND A PREPARING METHOD THEREOF

(76) Inventor: Si-Hoon Song, 550 Imsangdong, Iksan-si, Chollabuk-do 570-380 (KR)

( * ) Notice: Subject to any disclaimer, the term of this patent is extended or adjusted under 35 U.S.C. 154(b) by 0 days.

(21) Appl. No.: 09/914,964

(22) PCT Filed: Mar. 7, 2000

(86) PCT No.: PCT/KR00/00177

§ 371 (c)(1),
(2), (4) Date: Jan. 14, 2002

(87) PCT Pub. No.: WO00/53541

PCT Pub. Date: Sep. 14, 2000

(30) Foreign Application Priority Data

Mar. 9, 1999 (KR) ...................................... 1999-007707

(51) Int. Cl.$^7$ ................................................ A61K 9/14

(52) U.S. Cl. ...................................... 424/489; 424/464

(58) Field of Search ................................ 424/400, 464, 424/489

(56) References Cited

U.S. PATENT DOCUMENTS 6,284,709 B1  9/2001 Ju et al.
6,312,593 B1  11/2001 Petrie

*Primary Examiner*—Thurman K. Page
*Assistant Examiner*—Robert M. Joynes
(74) *Attorney, Agent, or Firm*—Muserlian, Lucas and Mercanti, LLP

(57) ABSTRACT

The present invention relates a composition promoting the growth, and increasing preservative capability of human body, animals and plants. The composition of the present invention maximizes physiological activity of human body, animals and plants. In addition, the present invention relates a producing method of the composition composed of the following steps: 1) preparing a composition containing kaoline (white soil) 30–40 wt %, potassium sulfate 15.0–20.0 wt %, sodium sulfate 13.0–17.0 wt %, feldspar 12.0–16.0 wt %, talc 12.0–16.0% and ferric oxide 0.5–1.5 wt %; and 2) mixing the above-mentioned composition using a compressed molding method; and 3) heating the mixed composition at 1000–1300° C.

The composition of the present invention can be used in whole fields of industries, and will cause the original changes in the field of industrial matters, and promote the welfare of human beings such as improvement of health and life of human.

8 Claims, No Drawings

COMPOSITION FOR INCREASING PRESERVATIVE CAPABILITY AND PROMOTING THE GROWTH OF LIVING ORGANISM AND A PREPARING METHOD THEREOF

This patent application claims a benefit of priority from Korean Patent Application No. 1999-0007707 filed Mar. 9, 1999 through PCT Application Serial No. PCT/KR00/00177, the contents of each of which are incorporated herein by reference.

FIELD OF THE INVENTION

The present invention relates to a composition promoting the growth of human body, animals and plants and increasing preservative capability of animals and plants.

The present invention also relates to a producing method of the composition composed of natural substances and compounds by mixing at almost the same ratio as that of inorganic substances in human, animals and plants.

The producing method of the present invention may be used in the whole field of industries such as building materials, home appliances, a medical industry and a food industry.

BACKGROUND

Natural substances such as yellow soil and silicon dioxide mineral, and synthetic ceramic have been used in the whole field of industries such as medical instruments using infrared-ray and home appliances.

However, since the above-mentioned things is prepared by using the natural substances such as yellow soil and white soil as major components, content of a silicate ($SiO_2$) is high, whereas contents of inorganic substances such as potassium, calcium, sodium, magnesium and iron are very low.

SUMMARY OF THE INVENTION

It is an object of this invention to provide a composition activating physiological activity of human body, animals and plants at a maximum level.

It is a further object of this invention to provide a producing method the composition.

DETAILED DESCRIPTION OF PREFERRED EMBODIMENTS

Potassium, calcium, sodium, magnesium and iron are major components of inorganic substances of human body, animals and plants. Thus, the composition of the present invention is prepared by mixing various components at almost the same ratio as that of inorganic components of animals and plants.

The composition of the present invention contains kaoline (white soil) 30.0–40.0 wt %, potassium sulfate 15.0–20.0 wt %, sodium sulfate 13.0–17.0 wt %, feldspar 12.0–16.0 wt %, talc 12.0–16.0% and ferric oxide 0.5–1.5 wt %. The composition is mixed by a compressed molding method with water, dried and manufactured in random forms. The resulting composition becomes plastic at 1000–1300° C. for its use in various forms.

The composition of the present invention prepared by the above-mentioned composition has components shown in the following Table 1.

TABLE 1

Average ratio of components of composition

| Components | Weight ratio(wt %) |
| --- | --- |
| Potassium(K) | 19.06–23.29 wt % |
| Calcium(Ca) | 14.21–17.36 wt % |
| Sodium(Na) | 12.30–14.97 wt % |
| Magnesium(Mg) | 11.98–14.64 wt % |
| Silicon(Si) | 13.74–16.80 wt % |
| Aluminum(Al) | 12.21–15.13 wt % |
| Iron(Fe) | 3.48–4.26 wt % |
| Titanium(Ti) | 0.95–1.17 wt % |
| Manganese(Mn) | 0.26–0.40 wt % |
| Zinc(Zn) | 0.17–0.20 wt % |
| Germanium(Ge) | 0.07–0.09 wt % |
| Selenium(Se) | 0.03–0.04 wt % |
| Other elements | 1.36–1.67 wt % |

The major components of the composition of the present invention are potassium, calcium, sodium and magnesium, which has similar distribution with inorganic substances of human body, animals and plants. In addition, the composition of the present invention has an affinity for silicon and aluminium abundantly contained in soil.

Whereas, as shown in Table 2, general ceramic products contain large amounts of silicon and aluminium, and small amounts of potassium, calcium, sodium and magnesium.

TABLE 2

Average ratio of components of general ceramic products

| Components | Weight ratio(wt %) |
| --- | --- |
| Aluminium(Al) | 35.36–43.22 wt % |
| Silicon(Si) | 31.33–38.30 wt % |
| Potassium(K) | 7.73–9.45 wt % |
| Magnesium(Mg) | 3.56–4.36 wt % |
| Iron(Fe) | 3.52–4.31 wt % |
| Calcium(Ca) | 3.40–4.16 wt % |
| Sodium(Na) | 2.79–3.63 wt % |
| Titanium(Ti) | 0.03–0.04 wt % |
| Other elements | 2.10–2.57 wt % |

The ratio of components of general yellow soil ceramic is shown in Table 3.

TABLE 3

Average ratio of components of general yellow soil ceramic

| Components | Weight ratio (wt %) |
| --- | --- |
| Silicon dioxide ($SiO_2$) | 64.08–79.42 wt % |
| Aluminium oxide (($Al_2O_3$)) | 9.45–11.55 wt % |
| Sodium oxide ($NaO_2$) | 3.32–4.02 wt % |
| Ferric oxide ($Fe_2O_3$) | 2.93–3.58 wt % |
| Potassium oxide ($K_2O$) | 2.22–2.71 wt % |
| Other elements | 8.02–9.80 wt % |

As shown in Table 3, the general yellow soil ceramic contains mostly silicon and aluminium as major components, and small amounts of potassium, calcium, sodium and magnesium which are associated with human body, animals and plants. Hereinafter, the present invention is described in detail.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of the Composition

The composition of the present invention contains the following components: i) Kaoline (white soil) 30–40wt %; ii) potassium sulfate 15.0–20.0 wt %; iii) sodium sulfate 13.0–17.0 wt %; iv) feldspar 12.0–16.0 wt %; v) talc 12.0–16.0%; and vi) ferric oxide 0.5–1.5 wt %.

In the above composition, potassium sulfate and sodium sulfate may be replaced by the same amounts of potassium chloride and sodium chloride ions. However, because a moisture drying efficiency of sulfate salts are better than that of chloride salts, the present inventors selected potassium sulfate and sodium sulfate to increase the moisture drying efficiency.

The composition was manufactured in form of minute powder of 100–150 mesh. After the composition was mixed by the compressed molding method or with 20–30 wt % of water to mold in the fixed form, it was dried by hot wind at 40–80° C. for 10–15 hours and heated 1000–1300° C. for 2–3 hours to be plastic. The manufactured composition was prepared in various forms to be used for various industry.

The composition of the present invention activated physiological activity of human body, animals and plants at a maximum level In addition, Such activation by the composition of the present invention was superior to that by conventional ceramic products.

Generally, infrared-ray irradiation of silicon is higher than that of potassium. Whereas, the composition of the present invention was excellent in biological effect on the living organisms.

Experiment 1

Physiological Reactivity of the Composition of the Present Invention and General Ceramic Products The present inventors performed the physiological reactivity experiment of the composition and general ceramic products, and compared their physiological reactivities. The result was shown in Table 4.

TABLE 4

| | The results of comparing the physiological reactivity. | | | |
|---|---|---|---|---|
| Item | Refinement velocity of coffee taste | Refinement velocity of tobacco | deordorization of Refrigerator | Freshness of vegetables |
| Yellow ceramic | 10 hours* (3 hours) | 10 hours* (3 hours) | No effect | No effect |
| Medical ceramic | 10 min* (20 sec) | 5 min* (5 sec) | From 2 hours after starting | 180% increase |
| Industrial ceramic | 5 hours* (1 hour) | 1 hour* (30 min) | From 5 hours after starting | 130% increase |
| The composition of the present invention | 30 sec* (10 sec) | 20 sec* (2 sec) | From 30 min after starting | 250% increase |

*the experiment was performed at room temperature, ( ): the experiment was performed at 50° C.

The composition of the present invention was superior to the conventional ceramic products in exerting much more advantageous effects on the living organisms more rapidly.

In addition, the composition was prepared in form of minute powder of 200–350 mesh and mixed with synthetic resin to the concentration of 5–30%. The resulting mixture can be used in various forms for industry.

For example, after the composition of the present invention was added to polyethylene film which has been used a vinyl house for cultivating plants, the present inventors cultivated the crops using the vinyl house made from the ployethylene film containing the composition of the present invention and the vinyl house made from general polyethylene film. The results was shown in Table 5.

TABLE 5

| | The results of cultivating the crops | | |
|---|---|---|---|
| | | Average yield | |
| crop | Polyethylene film | Polyethylene film containing the component | Comparison (increasing ratio) |
| Chinese cabbage | 416 kg | 499 kg | 20% increase |
| Cucumber | 422 kg | 527 kg | 25% increase |
| Tomato | 575 kg | 719 kg | 25% increase |
| Red pepper | 179 kg | 250 kg | 40% increase |

(increase per 100 m$^2$ of cultivation areas)

As shown in Table 5, when the synthetic resin containing the composition of the present invention was used, the yield of the crops was increased more about 20–40% than that when the general synthetic resin was used. Therefore, these results demonstrate that the composition of the present invention accelerates physiological activity of plants.

INDUSTRIAL APPLICABILITY

The composition of the present invention, can maximize physiological activity of the human body, animals and plants. Thus, the composition of the present invention can be used for industry and will cause the original changes in the field of industrial matters.

In detail, for example, the composition of the present invention can be used all the industries including building materials and raw materials of various synthetic resins (especially, vinyl, plastic, etc.), various food containers, cosmetics and cosmetics containers, various medical instruments (especially, medical instruments using far infrared-ray), medicines and medicines containers, containers for cultivating various plants, deodorants and chemical products such as agricultural chemicals. Therefore, it is expected that the composition of the present invention will promote the welfare of human beings such as improvement of health and life of human.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A composition comprising kaoline (white soil) 30.0–40.0 wt %, potassium sulfate 15.0–20.0 wt %, sodium sulfate 13.0–17.0 wt %, feldspar 12.0–16.0 wt %, talc 12.0–16.0 wt % and ferric oxide 0.5–1.5 wt %.

2. A composition comprising potassium 19.06–23.29 wt %, calcium 14.21–17.36 wt %, sodium 12.30–14.97 wt %, magnesium 11.98–14.64 wt %, silicon 13.74–16.80 wt %, aluminum 12.21–15.13 wt %, iron 3.48–4.26 wt %, titanium 0.95–1.17 wt %, manganese 0.28–0.40 wt %, zinc 0.17–0.20 wt %, germanium 0.07–0.09 wt %, selenium 0.03–0.04 wt %.

3. A method of preparing a composition, comprising the steps: 1) mixing kaoline (white soil) 30.0–40.0 wt %, potassium sulfate 15.0–20.0 wt %, sodium sulfate 13.0–17.0 wt %, feldspar 12.0–16.0 wt %, talc 12.0–16.0 wt % and ferric oxide 0.5–1.5 wt % using a compressed molding method; and 2) heating the mixture at 1000–1300° C.

4. A method of preparing a composition according to claim 3, wherein said heating is carried out for a time period of 2 to 3 hours.

5. A composition containing kaoline (white soil) 30.0–40.0 wt %, potassium chloride 15.0–20.0 wt %, sodium chloride 13.0–17.0 wt %, feldspar 12.0–16.0 wt %, talc 12.0–16.0 wt % and ferric oxide 0.5–1.5 wt %.

6. A composition according to claim 1, wherein said composition is prepared in the form of minute powder of 200–350 mesh and mixed with a synthetic resin.

7. The composition of claim 6, wherein the concentration of said resin is 5 to 30%.

8. A polyethylene film containing the composition of claim 1.

* * * * *